US006309639B1

(12) United States Patent
Cummings et al.

(10) Patent No.: US 6,309,639 B1
(45) Date of Patent: Oct. 30, 2001

(54) METHOD FOR INHIBITING AN INFLAMMATORY RESPONSE USING ANTIBODIES TO P-SELECTIN GLYCOPROTEIN LIGAND

(75) Inventors: Richard D. Cummings, Edmond; Kevin L. Moore; Rodger P. McEver, both of Oklahoma City, all of OK (US)

(73) Assignee: The Board of Regents of the University of Oklahoma

( * ) Notice: Subject to any disclaimer, the term of this patent is extended or adjusted under 35 U.S.C. 154(b) by 0 days.

(21) Appl. No.: 09/635,297

(22) Filed: Aug. 9, 2000

Related U.S. Application Data

(62) Division of application No. 09/207,375, filed on Dec. 8, 1998, now Pat. No. 6,177,547, which is a continuation of application No. 08/438,280, filed on May 10, 1995, now Pat. No. 5,852,175, which is a division of application No. 08/278,551, filed on Jul. 21, 1994, now Pat. No. 5,464,778, which is a continuation of application No. 07/976,552, filed on Nov. 16, 1992, now abandoned, which is a continuation-in-part of application No. 07/650,484, filed on Feb. 5, 1991, now abandoned.

(51) Int. Cl.$^7$ .......................... A61K 39/395; C07K 16/28

(52) U.S. Cl. .................................... 424/143.1; 424/130.1; 424/137.1; 424/141.1; 424/152.1; 424/172.1; 530/387.1; 530/387.5; 530/388.1; 530/388.2; 530/388.22; 530/389.1; 530/389.6

(58) Field of Search .............................. 530/387.1, 388.1, 530/387.5; 424/130.1, 152.1, 137.1

(56) References Cited

U.S. PATENT DOCUMENTS

| | | | |
|---|---|---|---|
| 3,625,214 | 12/1971 | Higuchi | 128/260 |
| 3,995,444 | 12/1976 | Clark et al. | 62/306 |
| 4,494,385 | 1/1985 | Kuraoka et al. | 62/306 |
| 4,783,330 | 11/1988 | Furie et al. | 424/1.1 |
| 4,849,513 | 7/1989 | Smith et al. | 536/27 |
| 4,906,474 | 3/1990 | Langer et al. | 424/428 |
| 4,925,673 | 5/1990 | Steiner et al. | 424/455 |
| 5,114,842 | 5/1992 | Plow et al. | 424/85.8 |
| 5,135,916 | 8/1992 | Sims et al. | 514/21 |
| 5,198,424 | 3/1993 | McEver et al. | 514/13 |
| 5,211,936 | 5/1993 | Brandley et al. | 424/1.1 |
| 5,240,833 | 8/1993 | Nudelman et al. | 435/70.21 |
| 5,378,464 | 1/1995 | McEver et al. | 424/143.1 |
| 5,464,778 | 11/1995 | Cummings et al. | 436/503 |
| 5,767,241 | 6/1998 | McEver | 530/350 |
| 5,827,817 | 10/1998 | Larsen et al. | 514/2 |
| 5,843,707 | 12/1998 | Larsen et al. | 435/69.1 |
| 5,852,175 | 12/1998 | Cummings et al. | 530/388 |
| 5,880,091 | 3/1999 | Cummings et al. | 514/8 |
| 5,919,637 | 7/1999 | McEver | 435/7.21 |
| 5,929,036 | 7/1999 | McEver | 514/25 |
| 6,177,547 | * 1/2001 | Cummings et al. | |

FOREIGN PATENT DOCUMENTS

| | | |
|---|---|---|
| 0153896 | 9/1985 | (EP) . |
| 9106632 | 5/1991 | (WO) . |
| 9107993 | 6/1991 | (WO) . |
| 9119501 | 12/1991 | (WO) . |
| 9201718 | 2/1992 | (WO) . |
| 9216612 | 10/1992 | (WO) . |
| 9305803 | 4/1993 | (WO) . |
| 9411498 | 5/1994 | (WO) . |
| 9530001 | 11/1995 | (WO) . |

OTHER PUBLICATIONS

Aruffo et al., "CD62/P–Selectin Recognition and Myeloid and Tumor Cell Sulfatides" *Cell*, 67:35–44 (1991).

Aulabaugh et al., "Conformational Analysis of Bombesin Analogues", *Peptides*, 526–528 (1990).

Battistutta et al. "Circular Dichroism and $^1$H NMR Studies on Bombolitin–related Peptides in Aqueous Solution Containing SDS Micelles", *Peptides* 525–526 (1992).

Beckstead et al., "Immunohistochemical Localization of Membrane and α–Granule Proteins in Human Megakaryocytes: Application to Plastic–Embedded Bone Marrow Biopsy Specimens", *Blood*, 67:285–293 (1986).

Bevilacqua et al., "Identification of an Inducible Endothelial Leukocyte Molecule", *Proc. Natl. Acad. Sci. USA*, 84:9238–9242 (1987).

Bevilaqua et al., "Endothelial Leukocyte Adhesion Molecule 1: An Inducible Receptor for Neutrophils Related to Complement Regulatory Proteins and Lectins", *Science*, 243:1160–1165 (Mar. 3, 1989).

Bienvenu et al., "Molecular Determinants of Shear Rate–Dependent Leukocyte Adhesion in Postcapillary Venule", *The American Physiology Society*, H1504–H1508 (1993).

Bierhuizen et al., "Expression of a Differentiation Antigen and Poly–N–acetyl actosaminyl O–glycans Directed by a Cloned Core 2 β–1, 6–N–Acetylglucosaminyltransferase", *The Journal of Biological Chemistry* 269(6):4473–4479 (1994).

Bonfanti et al., "PADGEM (GMP140) Is a Component of Weibel–Palade Bodies of Human Endothelial Cells," *Blood* 73:1109–112 (1989).

Borman S., "Glycotechnology Drugs Begin to Emerge from the Lab", *C& EN* 27–34 (Jun. 28, 1993).

Bowen et al., "Characterization of a Human Homologue of the Murine Peripheral Lymph Node Homing Receptor," *J. Cell Biol.*, 109:421–427 (Jul. 1989).

(List continued on next page.)

*Primary Examiner*—Phillip Gambel
(74) *Attorney, Agent, or Firm*—Dunlap, Codding & Rogers, P.C.

(57) ABSTRACT

P-selectin has been demonstrated to bind primarily to a single major glycoprotein ligand on neutrophils and HL-60 cells, when assessed by blotting assays and by affinity chromatography of [$^3$H]glucosamine-labeled HL-60 cell extracts on immobilized P-selectin. This molecule was characterized and distinguished from other well-characterized neutrophil membrane proteins with similar apparent molecular mass. The purified ligand, or fragments thereof (including both the carbohydrate and protein components), or antibodies to the ligand, or fragments thereof, can be used as inhibitors of binding of P-selectin to cells.

2 Claims, No Drawings

OTHER PUBLICATIONS

Brandley et al., "Carbohydrate Ligands of the LEC Cell Adhesion Molecules", *Cell*, 63:861–863.

Brockmeyer et al., "Distribution of Cell Adhesion Molecules (ICAM–1, VCAM–1, ELAM–1 in Renal Tissue During Allograft Rejection", *Transplantation* 55:610–615 (1993).

Burgen et al., "Binding of Flexible Ligands to Macromolecules", *Nature*, 253:753–755 (1975).

Buttrum et al., "Selectin–Mediated Rolling of Neutrophils on Immobilized Platelets", *Blood*, 83:1165–1174.

Colman et al., "Three–Dimensional Structure of a Complex of Antibody with Influenza Virus Neuraminidase", *Nature*, 326:358–363 (1987).

Corral et al., "Requirement for Sialic Acid on Neutrophils in a GMP–140 (PADGEM) Meidated Adhesive Interaction with Activated Platelets", Biochemical and Biophysical Research Communications, 172:1349–1356 (1990).

Cummings R., Untitled paper prepared at the University of Oklahoma Health Science Center, Mar. 23, 1995.

Damle et al., "GMP–140 (P–selectin/CD62) Binds to Chronically Stimulated but not Resting $CD4^+T$ Lymphocytes and Regulates Their Production of Proinflammatory Cytokines", *Eur. J. Immunol.*, 22:1789–1793 (1992).

Dawson et al., "The Monoclonal Antibody MEL–14 Can Block Lymphocyte Migration Into a Site of Chronic Inflammation", *Eur. J. Immunol.*, 1647–1650 (1992).

Doré et al., "P–Selectin Mediates Spontaneous Leukocyte Rolling In Vivo", *Blood*, 82:1308–1316 (1993).

Dorfman et al., "Human Transcription Factor GATA–2", *J. Biol. Chem.*, 267:1279–1285 (1992).

Dunlop et al., "Characterization of GMP–140 (P–selectin) as a Circulating Plasma Protein",*J. Exp. Med.*, 175:1147–1150 (1992).

Edwards et al, "The Role of Leukocytes in the Activation of Blood Coagulation", *Seminars in Hematology*, 29:202–212 (1992).

Engleberts et al., "Generalized Inflammation During Peritonitis Evidenced by Intracutaneous E–Selectin Expression", *Clinical Immunology and Immunopathology*, 65:330–334 (1992).

Engleberts et al., "A Role for ELAM–1 in the Pathogenesis of MOF during Septic Shock", *Journal of Surgical Research*, 53:136–144 (1992).

Franklin T., "Binding Energy and the Activation of Hormone Receptors", *Pharmacology*, 29:853–856 (1980).

Fukuda et al., "Structures of Sialylated Fucosyl Polylactosaminoglycans Isolated from Chronic Myelogenous Leukemia Cells," *J. of Biol. Chem*, 260(24):12957–12967 (1985).

Fukushi et al., "Novel Fucolipids Accumulating in Human Adenocarcinoma,"*J. of Biol. Chem.*, 259(16):10511–10517, (1984).

Fuggle et al., "Variation in Expression of Endothelial Adhesion Molecules in Pretransplant and Transplanted Kidneys–Correlation with Intragraft Events", *Transplantation*, 55:117–123 (1993).

Gamble et al., "Prevention of Activated Neutrophil Adhesion to Endothelium by Soluble Adhesion Protein GMP140", *Science*, 249:414–417 (1990).

Geng et al., "Lectin Domain Peptides from Selectins Interact with Both Cell Surface Ligands and $Ca^{2+}$ Ions", *J. Biol. Chem.*, 267:19846–19853 (1992).

Geng et al., "Rapid Neutrophil Adhesion to Activated Endothelium Mediated by GMP–140", *Nature* 343:757–760 (1990).

Gibbons et al., "New Mechanisms and Intermediates in the Folding and Unfolding of Peptides and Proteins: Bioactive solution Conformation of Linear Peptides", *Peptides*, 508–509 (1990).

Goelz et al., "ELFT: A Gene That Directs the Expression of an ELAM–1 Ligand," *Cell*, 63:1349–1356, (1990).

Grober et al., "Monocyte–Endothelial Adhesion in Chronic Rheumatoid Arthritis", *J. Clin. Invest.*, 91:2609–2619 (1993).

Hakomori S., "Aberrant Glycosylation in Cancer Cell Membranes as Focused on Glycolipids: Overview and Perspectives", *Cancer Research*, 45:2405–2414 (1985).

Hamburger et al., "GMP–140 Mediates Adhesion of Stimulated Platelets to Neutrophils", *Blood*, 75:550–554 (1990).

Handa et al., "Selectin GMP–140 (CD62; PADGEM) Binds to Sialosyl–$Le^x$, and Sulfated Glycans Modulate this Binding", *Biochemical and Biophysical Research Communications*, 181:1223–1230 (1991).

Hard et al., "The Carbohydrate Chains of the $\beta$ Subunit of Human Chorionic Gonadotropin Produced by the Choriocarcinoma Cell Line BeWo", *Eur. J. Biochem*, 205:785–798 (1992).

Hattori et al., "Complement Proteins C5b–9 Induce Secretion of High Molecular Weight Multimers of Endothelial von Willebrand Factor and Translocation of Granule Membrane Protein GMP–140 to the Cell Surface",*J. Biol. Chem.*, 264:9053–9060 (1989).

Hattori et al., "Stimulated Secretion of Endothelial von Willebrand Factor is Accompanied by Rapid Redistribution to the Cell Surface of the Intracellular Granule Membrane Protein GMP–140",*J. Biol. CHem.* 264:7768–7771 (1989).

Hemmerich et al., "Structure of the O–Glycans in Bly-CAM–1, and Endothelial–derived Ligand for L–selectin", *The Journal of Biological Chemistry* 270(20):12035–12047 (1995).

Hoff et al., "Increased Expression of Sialyl–Dimeric $Le^x$ Antigen in Liver Metastases of Human Colorectal Carcinoma", *Cancer Research*, 49:6883–6888 (1989).

Hollengaugh et al., "Interaction of P–Selectin (CD62) and Its Cellular Ligand: Analysis of Critical Residues" *Biochemistry*, 32:2960–2966 (1993).

Huang et al., "A Lymphocyte Homing Receptor (L–Selectin) Mediates the In Vitro Attachment of Lymphocytes to Myelinated Tracts of the Central Nervous System",*J. Clin. Invest.*, 88:1778–1783 (1991).

Jewell et al., "Cytokine Induction of Leucocyte Adhesion Molecules–1 (LAM–1) Expression on Chronic Lymphocytic Leukaemia Cells", *Leukemia* 6(5):400–404 1992).

Johnston et al., "Cloning of GMP–140: Chromosomal Localization, Molecular Heterogeneity and Identification of cDNAs Predicting Both Membrane Bound and Soluble Proteins", *Blood Suppl.*, 72:327a (1988).

Johnston et al., "Cloning of GMP–140, a Granule Membrane Protein of Platelets and Endothelium: Sequence Similarity to Proteins Involved in Cell Adhesion and Inflammation", *Cell*, 56:1033–1044 (1989).

Johnston et al., "Structural and Biosynthetic Studies of the Granule Membrane Protein, GMP–140, from Human Platelets and Endothelial Cells", *The Journal of Biological Chemistry*, 264:1–8 (1989).

Johnston et al., Structure and Biosynthesis of the Platelet α–Granule Membrane Protein, GMP–140, *Platelets*, p. 352a, abstract # 1264.

Johnston et al., "*Structure of the Human Gene Encoding Granule Membrane Protein–140, a member of the Selectin Family of Adhesion Receptors for Leukocytes*", The Journal of Biological Chemistry 265(34):21381–21385 (1990).

Jungi et al., "Platelet–Leukocyte Interaction: Selective Binding of Thrombin–Stimulated Platelets to Human Monocytes, Polymorphonuclear Leukocytes, and Related Cell Lines", *Blood* 67(3):629–636 (1986).

Kijima–Suda et al., "Possible Mechanism of Inhibition of Experimental Pulmonary Metastasis of Mouse Colon Adenocarcinoma 26 Sublines by a Sialic Acid:Nucleosides Conjugate," *Cancer Research*, 48:3728–3732, (Jul. 1, 1998).

Kojima et al., "Inhibition of Selectin–Dependent Tumor Cell Adhesion to Endothelial Cells and Platelets by Blocking O–Glycosylation of These Cells", *Biochemical and Biophysical Research Communication*, 182(3):1288–1295 91992).

Korrel et al., "Identification of Tetrasialyated Monofucosylated Tetraantennary N–linked Carbohydrate Chain in Human Platelet Glycocalin," *FEBS Letters*, 228(2):321–326, (Feb. 1988).

Laczko–Hollosi et al., "Conformational Change of a Synthetic Amyloid Analogue des[Ala$^{21,30}$]A42 Upon Binding to Octyl Glucoside Micelles," *Peptides*, 527–528, (1992).

Laiken et al., "A New Model for the Binding of Flexible Ligands to Proteins", *Biochemistry*, 10:2101–2106 (1971).

Larsen et al., "PADGEM Protein: A Receptor That Mediates the Interaction of Activated Platelets with Neutrophils and Monocytes," *Cell*, 59:305–312, (Oct. 20, 1989).

Larsen et al., "PADGEM–Dependent Adhesion of Platelets to Monocytes and Neutrophils Is Mediated by a Lineage–Specific Carbohydrate, LNF III (CD15)", *Cell*, 63:467–474 (1990).

Lasky et al., "Cloning of a Lymphocyte Homing Receptor Reveals a Lectin Domain," *Cell*, 56:1045–1055, (Mar. 24, 1989).

Lawrence et al., "Leukocytes Roll on a Selectin at Physiologic Flow Rates: Distinction from and Prerequisite for Adhesion through Integrins", *Cell*, 65:1–20 (1991).

Levinovitz et al., "Identification of a Glycoprotein Ligand for E–Selectin on Mouse Myeloid Cells", *The Journal of Cell Biology*, 121(2):449–459 (1993).

Ley et al., "Lectin–Like Cell Adhesion Molecule 1 Mediates Leukocyte Rolling in Me senteric Venules In Vivo", *Blood*, 77(12):2553–2555 (1991).

Li et al., "T Cells Expressing Both L–Selectin and CD44 Molecules Increase in Number in Peritoneal Exudate Cells and In Vitro–Stimulated Spleen Cells from Mice Immunized Intraperitoneally with Listeria Monocytogenes", *Immunology*, 78:28–34 (1993).

Liao et al, "Oxidized Lipoproteins, Elicit Leukocyte–Endothelial Cell Adhesion in Mesenteric Venules", *The FASEB Journal*, 7(3):1986 (1993).

Lowe et al., "ELAM–1–Dependent Cell Adhesion to Vascular Endothelium Determined by a Transfected Human Fucosyltransferase cDNA," *Cell*, 63:475–484, (Nov. 2, 1990).

Lowe et al., "A Transfected Human Fucosyltransferase cDNA Determines Biosynthesis of Oligosaccharide Ligand(s) for Endothelial–Leukocyte Adhesion Molecule 1", *Biochemical Society Transaction*, 19:649–653 (1991).

Maemura et al, "Poly–N–Acetyllactosaminyl O–Glycans Attached to Leukosialin", *The Journal of Biological Chemistry*, 267(34):24379–24386 (1992).

Majuri et al., "Recombinant E–selectin–protein Mediates Tumor Cell Adhesion via Sialyl–Lea and Sialyl–Lex", *Biochemical and Biophysical Research Communications*, 182(3):1376–1382 (1992).

Mayadas et al., "Leukocytes Rolling and Extravasation Are Severely Compromised in P Selectin–Deficient Mice", *Cell*, 74:541–554 (1993).

McEver et al., "GMP–140 a Platelet α–Granule Membrane Protein, Is Also Synthesized by Vascular Endothelial Cells and Is Localized in Weibel–Palade Bodies," *J. Clin. Invest.*, 84:92–99, (Jul. 1989).

McEver R., "GMP–140: A Receptor for Neutrophils and Monocytes on Activated Platelets and Endothelium," *J. of Cell Biochem*, 45:156–161 (1991).

McEver R., "Editorial: Misguided Leukocyte Adhesion," *J. Clin. Invest.*, 91:2340–2341, (Jun . 1993).

McEver R., "The Platelet α–Granule Membrane Protein GMP–140 is also Synthesized by Human Vascular Endothelial Cells and is Present in Blood Vessels of Diverse Tissues," *Blood Suppl.*, 70:355a, (Nov. 1987).

McEver R., "Leukocyte–Endothelial Cell Interactions", *Current Opinion in Cell Biology*, 4:840–849 (1992).

McEver et al., "A Monoclonal Antibody to a Membrane Glycoprotein Binds Only to Activated Platelets", *The Journal of Biological Chemistry*, 259(15):9799–9804 (1984).

McEver R., "Properties of GMP–140–, an Inducible Granule Membrane Protein of Platelets and Endothelium", *Blood Cells*, 16:73–83 (1990).

McEver R., "Selectins: Novel Receptors that Mediate Leukocyte Adhesion During Inflammation", *Thrombosis and Haemostasis*, 65(3):223–228 (1991).

Mengelers et al., "Down Modulation of L–Selectin Expression on Eosinophils Recovered from Bronchoalveloar Lavage Fluid After Allergen Provocation," *Clinical and Experimental Allergy*, 23:196–204, (1993).

Montefort et al., "The Expression of Leukocyte–Endothelial Adhesion Molecules Is Increased in Perennial Allergic Rhinitis," *Am. J. Respir. Cell Mol. Biol.*, 7:393–398, (1992).

Moore et al., "GMP–140 Binds to a Glycoprotein Receptor on Human Neutrophils: Evidence for a Lectin–Like Interaction", *The Journal of Cell Biology*, 112(3):491–499 (1991).

Moore et al., "Identification of a Specific Glycoprotein Ligand for P–Selectin (CD62) on Myeloid Cells", *The Journal of Cell Biology*, 118(2):445–456 (1992).

Moore et al., "P–Selectin (CD62) Binds to Subpopulations of Human Memory T Lymphocytes and Natural Keller Cells", *Biochemical and Biophysical Research Communications*, 186(1);173–181 (1992).

Mulligan et al., "Neutrophil–Dependent Acute Lung Injury," *J. Clin. Invest.*, 90:1600–1607, (Oct. 1992).

Mulligan et al., "Protective Effects of Oligosaccharides in P–Selectin–Dependent Lung Injury", *Nature* 364:149–151 (1993).

Mulligan et al., "Role of Endothelial–Leukocyte Adhesion Molecule 1 (ELAM–1) in Neutrophil–Mediated Lung Injury in Rats," *J. Clin. Invest.*, 88:1396–1406, (Oct. 1991).

Munro et al., "Expression of Sialyl–Lewis X, and E–Selectin Ligand, IN Inflammation, Immune Processes, and Lymphoid Tissues", *American Journal of Pathology*, 141(6):12397–1408 (1992).

Nelson et al., "Higher–Affinity Oligosaccharide Ligands for E–Selectin", *J. Clin. Invest.*, 91:1157–1166 (1993)l.

Newman et al., "Soluble E–Selectin is Found in Supernatants of Activated Endothelial Cells and Is Elevated in the Serum of Patients with Septic Shock," *J. of Immun.*, 150(2):644–654, (Jan. 15, 1993).

Norgard et al., "Characterization of a Specific Ligand for P–Selectin on Myeloid Cells: A Minor Glycoprotein with Sialylated O–linked Oligosaccharides", *The Journal of Biological Chemistry*, 268(18):12764–12774 (1993).

Norton et al., "Expression of Adhesion Molecules in Human Intestinal Graft–Versus–Host Disease," *Clin. Exp. Immunol.*, 87:231–236, (1992).

Ockenhouse et al., "Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1," *J. of Exp. Med.*, 176:1183–1189, (Oct. 1992).

Ord et al., "Structure of the Gene Encoding the Human Leukocyte Adhesion Molecule–1 (TQ1, Leu–8) of Lymphocytes and Neutorphils," *J. Biol. Chem.*, 265(14):7760–7767, (May 15, 1990).

Paik et al., "Nucleotide Sequence and Structure of the Human Apolipoprotein E Gene," *Proc. Natl. Acad. Sci. USA*, 82:3445–3449, (May 1985).

Palabrica et al., "Leukocyte Accumulation Promoting Fibrin Deposition Is Mediated In Vivo by P–selectin on Adherent Platelets," *Nature*, 359:848–851, (Oct. 29, 1992).

Pan et al., "Identification of a Promoter Region in the Human GMP–140 Gene that Confers Tissue–Specific Expression," *Blood*, 78(10):279A, (1991).

Pan et al., "Characterization of the Promoter for the Human P–selectin Gene," *J. of Biol. Chem.*, 268(30):22600–26609, (1993).

Patel et al., "Oxygen Radicals Induce Human Endothelial Cells to Express GMP–140 and Bind Neutrophils," *J. of Cell Biol.*, 112(4):749–759, (Feb. 1991).

Phillips et al, "ELAM–1 Mediates Cell Adhesion by Recognition of a Carbohydrate Ligand, Sialyl–Le", *Science* 250:1130–1132 (1990).

Polley et al., "CD62 and Endothelial Cell–Leukocyte Adhesion Molecule 1 (ELAM–1) Recognized the Same Carbohydrate Ligand, Sialyl–Lewis X", *Proc. Natl. Acad. Sci. USA*, 88:6224–6228 (1991).

Postigo et al., "Increased Binding of Synovial T Lymphocytes from Rheumatoid Arthritis to Endothelial–Leukocyte Adhesion Molecule–1 (ELAM–1) and Vascular Cell Adhesion Molecule–1 (VCAM–1)," *J. Clin. Invest.*, 89:1445–1452, (May 1992).

Rinder et al., "Cardiopulmonary Bypass Induces Leukocyte– Platelet Adhesion," *Blood*, 79(5):1201–1205, (Mar. 1, 1992).

Rini et al., "Structural Evidence for Induced Fit as a Mechanism for Antibody–Antigen Recognition," *Science*, 255(5047):959–965, (1992).

Rosen S., "The LEC–CAMs: An Emerging Family of Cell–Cell Adhesion Based Upon Carbohydrate Recognition," *Am. J. Respir. Cell. Mol. Biol.*, 3:397–402, (1990).

Ruoslahti et al., "New Perspective in Cell Adhesion: RGD and Integrins," *Science*, 238:481–497, (1987).

Sanders et al., "Molecular Cloning and Analysis of In Vivo Expression of Murine P–Selectin," *Blood*, 80(3):795–800, (Aug. 1, 1992).

Shreeniwas et al., "Hypoxia–Mediated Induction of Endothelial Cell Interleukin–1α," *J. Clin. Invest.*, 90:2333–2339, (Dec. 1992).

Siegelman et al., "Mouse Lymph Node Homing Receptor cDNA Clone Encodes a Glycoprotein Revealing Tandem Interaction Domains," *Science*, 243:1165–172, (Mar. 3, 1989).

Siegelman et al., "Human Homologue of Mouse Lymph Node Homing Receptor: Evolutionary Conservation at Tandem Cell Interaction Domains," *Proc. Natl. Acad. Sci. USA*, 86:5562–5566, (Jul. 1989).

Siligardi et al., "Correlations Between Biological Activities and Conformational Properties of Elactonin and Porcine Calcitonin Elucidated by CD," *Petides 1992*, 553–554, (1993).

Simmons et al., "Sialyl Ligands Facilitate Lymphocyte Accumulation During Inflammation of the Central Nervous System", *Journal of Neuroimmunology*, 41:123–130 (1992).

Skinner et al., "Characterization of Human Platelet GMP–140 as a Heparin–Binding Protein," *Biochem. and Biohpys. Res. Comm.*, 164(3):1373–1379, (Nov. 15, 1989).

Skinner et al, "GMP–140 Binding to Neutrophils Is Inhibited by Sulfated Glycans", *The Journal of Biological Chemistry*, 266(9):5371–5374 (1991).

Spertini et al., "Monocyte Attachment to Activated Human Vascular Endothelium In Vivo Is Mediated by Leukocyte Adhesion Molecule–1 (L–Selectin) under Nonstatic Conditions," *J. Exp. Med.*, 175(6):1789–1792, (1992).

Spooncer et al., "Isolation and Characterization of Polyfucosylated Lactosaminoglycan from Human Granulocytes," *J. of Biol. Chem.*, 259(8):4792–4801, (1984).

Springer et al., "Sticky Sugars for Selectins," *Nature*, 349:196–197, (Jan. 17, 1991).

Stanley et al., "The LEC11 Chinese Hamster Ovary Mutant Synthesizes N–Linked Carbohydrates Containing Sialylated Fucosylated Lactosamine Units Analysis by One– and Two–Dimensional $^1$H NMR Spectroscopy," *J. of Biol. Chem.*, 263(23):11374–11381, (Aug. 15, 1988).

Steinhoff et al., "Expression Patterns of Leukocyte Adhesion Ligand Molecules on Human Liver Endothelia," *Am. Jour. of Path.*, 142(2):481–488, (1993).

Steininger et al., "The Glycoprotease of *Pasteurella haemolytica* A1 Eliminates Binding of Myeloid Cells to P–Selectin but not to E–Selectin," *Biochem. and Biophys. Rese. Comm.*, 188(2):760–766, (Oct. 30, 1992).

Stenberg et al., "A Platelet Alpha–Granule Membrane Protein (GMP–140) Is Expressed on the Plasma Membrane after Activation," *J. of Cell Biol.*, 101:880–86, (Sep. 1985).

Stone et al., "P–Selectin Mediates Adhesion of Platelets to Neuroblastoma and Small Cell Lung Cancer," *J. Clin. Invest.*, 92:804–813, (Aug. 1993).

Takada et al., Adhesion of Human Cancer Cells to Vascular Endothelium Mediated , *Biochemical and Biophysical Research Communications*, 179(2):713–719 (1991).

Takada et al., "Contribution of Carbohydrate Antigens Sialyl Lewis A and Sialyl Lewis X to Adhesion of Human Cancer Cells to Vascular Endothelium," *Cancer Research*, 53:354–361, (1993).

Taylor J., "Conformation Induction in Amphiphilic Peptide Hormones Bound to Model Interfaces," *Pept: Chem. Struct. Biol., Proc. Am. Pept. Symp. 11$^{th}$*, 592–594, (1990).

Tedder et al., "Isolation and Chromosomal Localization of cDNAs Encoding a Novel Human Lymphocytes Cell Surface Molecule, LAM–1," *J. Exp. Med.*, 170:123–133, (Jul. 1989).

Thierry et al., "Intracellular Availability of Unmodified, Phosphorothioated and Liposomally Encapsulated Oligodeoxynucleotides for Antisense Activity," *Nucleic Acids Research*, 20(21):5691–5698, (1992).

Tiemeyer et al., "Carbohydrate Ligands for Endothelial–Leukocyte Adhesion Molecule 1", *Proc. Natl. Acad. Sci. USA*, 88:1138–1142 (1991).

Till et al., "Adhesion Molecules in Experimental Phacoanaphylactic Endophthalmitis," *Investigative Ophthalmology & Visual Science*, 33(12):3417–3423, (1992).

Todderud et al., "Soluble GMP–140 Inhibits Neutrophil Accumulation in Induced Murine Peritonitis," *FASEB Journal*, 6(4):5513, (1992).

van der Wal et al., "Adhesion Molecules on the Endothelium and Mononuclear Cells in Human Atherosclerotic Lesions," *Amer. J. of Path.*, 141(6):1427–1433, (1992).

Varki, "Selectin Ligands," *Proc. Natl. Acad. Sci. USA*, 91:7390–7397, 1994.

Volpes et al., "Vascular Adhesion Molecules in Acute and Chronic Liver Inflammation," *Hepatology*, 15(2):269–275, (1992).

von Andrian et al., "Two Step Model for Leukocyte–Endothelial Cell Interaction in Inflammation: Distinct Roles for LECAM–1 and the Leukocyte β2 Integrins In Vivo," *Proc. Natl. Acad. Sci.*, 88(17):7538–42, (Sep. 1, 1991).

Walz et al., "Recognition by ELAM–1 of the Sialyl–Le$^x$ Determinant on Myeloid and Tumor Cells", *Science*, 250:1132–1135 (1990).

Watson et al., "Genomic Organization of the Selectin Family of Leukocyte Adhesion Molecules on Human and Mouse Chromosome 1," *J. Exp. Med.*, 172:263–272, (Jul. 1990).

Watson et al., "Neutrophil Influx Into an Inflammatory Site Inhibition by a Soluble Homing Receptor–IgG Chimaera," *Nature*, 349:164–167, (Jan. 10, 1991).

Weyrich et al., "In Vivo Neutralization of P–Selectin Protects Feline Heart and Endothelium in Myocardial Ischemia and Reperfusion Injury," J. Clin. Invest., 91:2620–2629, (Jun. 1993).

Winn et al., "Anti–P–Selectin Monoclonal Antibody attenuates Reperfusion Injury to the Rabbit Ear", *J. Clin. Invest.*, 92:2042–2047 (1993).

Winn et al., "Monoclonal Antibodies to P–Selectin Are Effective in Preventing Reperfusion Injury to Rabbit Ears", *Supplement I Circulation*, 86(4):0316 (1992).

Zhou et al., "The Selectin GMP–140 Binds to Sialylated, Fucosylated Lactosaminoglycans on Both Myeloid and Monmyeloid Cells", *The Journal of Cell Biology*, 115(2):557–564 (1991).

* cited by examiner

METHOD FOR INHIBITING AN INFLAMMATORY RESPONSE USING ANTIBODIES TO P-SELECTIN GLYCOPROTEIN LIGAND

This is a divisional of U.S. Ser. No. 09/207,375, filed Dec. 8, 1998, now U.S. Pat. No. 6,177,547; which is a continuation of U.S. Ser. No. 08/438,280, filed May 10, 1995, now U.S. Pat. No. 5,852,175, issued on Dec. 22, 1998; which is a divisional of U.S. Ser. No. 08/278,551, filed Jul. 21, 1994, now U.S. Pat. No. 5,464,778, issued on Nov. 7, 1995; which is a continuation of U.S. Ser. No. 07/976,552, filed Nov. 16, 1992, now abandoned; which is a continuation-in-part of U.S. Ser. No. 07/650,484, filed Feb. 5, 1991, now abandoned.

The United States government has rights in this invention as a result of National Institutes of Health grants HI. 34363 (R. P. McEver) and HL 45510 (R. P. McEver and K. L. Moore), CA 38701 (A. Varki), IT4 RR 05351 (R. D. Cummings), and GM 45914 (D. F. Smith).

BACKGROUND OF THE INVENTION

P-selectin (CD62, GMP-140, PADGEM), a $Ca^{2+}$-dependent lectin on activated platelets and endothelium, functions as a receptor for myeloid cells by interacting with sialylated, fucosylated lactosaminoglycans. P-selectin binds to a limited number of protease-sensitive sites on myeloid cells, but the protein(s) that carry the glycans recognized by P-selectin are unknown. Blotting of neutrophil or HL-60 cell membrane extracts with [$^{125}$I]P-selectin and affinity chromatography of [$^3$H]glucosamine-labeled HL-60 cell extracts were used to identify P-selectin ligands. A major ligand was identified with an approximately 250,000 $M_r$ under nonreducing conditions and approximately 120,000 under reducing conditions. Binding of P-selectin to the ligand was $Ca^{2+}$ dependent and was blocked by mAbs to P-selectin. Brief sialidase digestion of the ligand increased its apparent molecular weight; however, prolonged digestion abolished binding of P-selectin. Peptide:N-glycosidase F treatment reduced the apparent molecular weight of the ligand by approximately 3,000 but did not affect P-selectin binding. Western blot and immunodepletion experiments indicated that the ligand was not lamp-1, lamp-2, or L-selectin, which carry sialyl Le$^x$, nor was it leukosialin, a heavy sialylated glycoprotein of similar molecular weight. The preferential interaction of the ligand with P-selectin suggests that it may play a role in adhesion of myeloid cells to activated platelets and endothelial cells.

The selectins are three structurally related membrane glycoproteins that participate in leukocyte adhesion to vascular endothelium and platelets, as reviewed by McEver, "Leukocyte interactions mediated by selecting" *Thromb. Haemostas.* 66:80–87 (1991). P-selectin (CD62), previously known as GMP-140 or PAD-GEM protein, is a receptor for neutrophils, monocytes and subsets of lymphocytes that is rapidly translocated from secretory granule membranes to the plasma membrane of activated platelets, as reported by Hamburger and McEver, "GMP 140 mediates adhesion of stimulated platelets to neutrophils" *Blood* 75:550–554 (1990); Larsen et al., "PADGEM protein: a receptor that mediates the interaction of activated platelets with neutrophils and monocytes" *Cell* 59:305–312 (1989) and endothelial cells, as reported by Geng et al., "Rapid neutrophil adhesion to activated endothelium mediated by GMP-140" *Nature* 343:757–760 (1990); Lorant et al., "Coexpression of GMP 140 and PAF by endothelium stimulated by histamine or thrombin: A juxtacrine system for adhesion and activation of neutrophils" *J. Cell Biol.* 115:223–234 (1991).

E-selectin (ELAM-1) is a cytokine-inducible endothelial cell receptor for neutrophils, as reported by Bevilacqua et al., "Identification of an inducible endothelial leukocyte adhesion molecule" *Proc. Natl. Acad. Sci. USA* 84:9238–9242 (1987), monocytes, as reported by Hession et al., "Endothelial leukocyte adhesion molecule 1: Direct expression cloning and functional interactions" *Proc. Natl. Acad. Sci. USA*. 87:1673–1677 (1990), and memory T cells, as reported by Picker et al., "ELAM-1 is an adhesion molecule for skin homing T cells" *Nature* (*London*) 349:796–799 (1991); Shimizu et al., "Activation-independent binding of human memory T cells to adhesion molecule ELAM 1" *Nature* (*London*) 349:799–802 (1991). L-selectin (LAM-1, LECAM-1), a protein expressed on myeloid cells and most lymphocytes, participates in neutrophil extravasation into inflammatory sites and homing of lymphocytes to peripheral lymph nodes, as reported by Lasky et al., "Cloning of a lymphocyte homing receptor reveals a lectin domain" *Cell* 56:1045–1055 (1989); Siegelman et al., "Mouse lymph node homing receptor cDNA clone encodes a glycoprotein revealing tandem interaction domains" *Science* (*Wash.DC*) 243:1165–1172 (1989); Kishimoto et al., "Neutrophil Mac-1 and MEL-1 adhesion proteins inversely regulated by chemotactic factors" *Science* (*Wash. DC*) 245:1238–1241 (1989); Watson et al., "Neutrophil influx into an inflammatory site inhibited by a soluble homing receptor IgG chimaera" *Nature* (*London*) 349:164–167 (1991).

Each selectin functions as a $Ca^{2+}$-dependent lectin by recognition of sialylated glycans. Both E- and P-selectin interact with sialylated, fucosylated lactosaminoglycans on opposing cells, including the sialyl Le$^x$ tetrasaccharide, as reported by Phillips et al., "ELAM 1 mediates cell adhesion by recognition of a carbohydrate ligand, sialy-Le$^x$" *Science* (*Wash. DC*) 250:1130–1132 (1990); Walz et al., "Recognition by ELAM-1 of the sialyl-Le$^x$ determinant on myeloid and tumor cells" *Science* (*Wash. DC*) 250:1132–1135 (1990); Lowe et al., "ELAM 1 dependent cell adhesion to vascular endothelium determined by a transfected human fucosyltransferase cDNA" *Cell* 63:475–484 (1990); Tiemeyer et al., "Carbohydrate ligands for endothelial-leukocyte adhesion molecule 1" *Proc. Natl. Acad. Sci. USA* 88:1138–1142 (1991); Goelz et al., "ELFT: a gene that directs the expression of an ELAM-1 ligand" *Cell* 63:1349–1356 (1990); Polley et al., "CD62 and endothelial cell-leukocyte adhesion molecule 1 (ELAM 1) recognize the same carbohydrate ligand. sialyl-Lewis x" *Proc. Natl. Acad. Sci. USA* 88:6224–6228 (1991); Zhou et al., "The selectin GMP-140 binds to sialyated, fucosylated lactosaminoglycans on both myeloid and nonmyeloid cells" *J. Cell Biol.* 115:557–564 (1991). However, the precise carbohydrate structures on myeloid cells recognized by these two selectins under physiologic conditions are not known. Such ligands might have unique structural features that enhance the binding specificity and/or affinity for their respective receptors.

P-selectin isolated from human platelets binds with apparent high affinity to a limited number of sites on neutrophils (Moore et al., "GMP 140 binds to a glycoprotein receptor on human neutrophils: evidence for a lectin-like interaction" *J. Cell Biol.* 112:491–499 (1991); Skinner et al., "GMP-140 binding to neutrophils is inhibited by sulfated glycans" *J. Biol. Chem.* 266:5371–5374 (1991) and HL-60 cells (Zhou et al., "The selectin GMP-140 binds to sialyated, fucosylated lactosaminoglycans on both myeloid and nonmyeloid cells" *J. Cell Biol.* 115:557–564 (1991)). Binding is abolished by treatment of the cells with proteases (Moore et al., 1991), suggesting that the glycans on myeloid cells recognized preferentially by P-selectin are on glycoprotein(s) rather than on glycolipids. The number of binding sites for platelet P-selectin on neutrophils has been estimated at 10,000–20,000 per cell (Moore et al., 1991; Skinner et al., 1991), suggesting that these sites constitute a small component of the total cell surface protein. The protein portion of this ligand(s) may be crucial for binding by presenting the glycan in an optimal configuration, clustering glycans to enhance avidity, favoring the formation of specific oligosaccharide structures by cellular glycosyltransferases or modifying enzymes, and/or stabilizing the lectin-carbohydrate interaction through protein-protein interactions with P-selectin.

The potential importance of protein components in enhancing ligand affinity is supported by studies of CHO cells transfected with a specific fucosyltransferase (Zhou et al., 1991). These cells express higher amounts of the sialyl Le$^x$ antigen than do HL-60 cells and have protease-sensitive binding sites for P-selectin. However, the interaction of P-selectin with these sites is of much lower apparent affinity than with those on myeloid cells, and adhesion of transfected CHO cells to immobilized P-selectin is weaker than that of neutrophils and HL-60 cells (Zhou et al., 1991). These observations suggest that myeloid cells express one or more membrane glycoproteins not found on CHO cells that enhance the lectin-mediated interaction with P-selectin. Alternatively, myeloid cells may express a glycosyltransferase or modifying enzyme not present in CHO cells.

It is therefore an object of the present invention to identify and characterize a specific glycoprotein ligand for P-selectin (CD62).

It is a further object of the present invention to provide methods and compositions derived from the characterization of a specific glycoprotein ligand for P-selectin for use in modifying inflammatory processes and in diagnostic assays.

SUMMARY OF THE INVENTION

P-selectin has been demonstrated to bind primarily to a single major glycoprotein ligand on neutrophils and HL-60 cells, when assessed by blotting assays and by affinity chromatography of [$^3$H]glucosamine-labeled HL-60 cell extracts on immobilized P-selectin. This molecule was characterized and distinguished from other well-characterized neutrophil membrane proteins with similar apparent molecular mass.

The purified ligand, or fragments thereof (including both the carbohydrate and protein components), or antibodies to the ligand, or fragments thereof, can be used as inhibitors of binding of P-selectin to cells.

DETAILED DESCRIPTION OF THE INVENTION

U.S. Ser. No. 07/554,199 filed Jul. 17, 1990 entitled "Peptides Selectively Interacting with Selectins" by Rodger P. McEver, described the ability of P-selectin (GMP-140) to mediate cell-cell contact by binding-to carbohydrate ligands on target cells and specific binding to protease-sensitive sites on human neutrophils. Studies with antibodies and with neuraminidase indicated that P-selectin bound to carbohydrate structures related to sialylated, fucosylated lactosaminoglycans. As described in U.S. Ser. No. 07/650,484 entitled "Ligand for GMP-140 Selectin and Methods of Use Thereof" filed Feb. 5, 1991 by Rodger P. McEver, P-selectin was also demonstrated to bind to sialylated, fucosylated lactosaminoglycans (including the tetrasaccharide sialyl Lewis x (sLe$^x$)) on both myeloid and nonmyeloid cells.

The ability of proteases to abolish P-selectin binding to neutrophils indicated that high affinity binding of P-selectin to myeloid cells occurred through interactions with cell surface glycoprotein(s) rather than with glycolipids. As also described in U.S. Ser. No. 07/650,484, P-selectin bound preferentially to a glycoprotein in human neutrophil extracts of Mr 120,000, as analyzed by SDS-PAGE under reducing conditions. The glycoprotein was partially purified on a P-selectin affinity column. It appeared to be heavily glycosylated because it stained poorly with silver and Coomassie blue. It appeared to be heavily sialylated because it bound to a wheat germ agglutinin affinity column. Treatment of the glycoprotein ligand with low doses of sialidase slowed its mobility on SDS gels, a pattern consistent with partial desialylation of heavily O-glycosylated proteins. Binding of P-selectin to the glycoprotein ligand was Ca$^{2+}$-dependent, blocked by monoclonal antibodies to P-selectin that also block P-selectin binding to leukocytes, and abolished by extensive treatment of the ligand with sialidase.

The preferential binding of P-selectin to the 120,000 D glycoprotein ligand in myeloid cell extracts suggested that it contained special structural features that are recognized with high affinity by P-selectin. Such structures might not be present on every protein or lipid characterized by sialylated, fucosylated structures such as sLe$^x$. It has now been further demonstrated that the adhesion of myeloid cells to immobilized P-selectin is much stronger than that to NeoLewis CHO cells (a cell line expressing sialylated, fucosylated lactosaminoglycans, described in U.S. Ser. No. 07/650,484), even though the NeoLewis cells express higher levels of sLe$^x$ antigen, as reported by Zhou et al., *J. Cell Biol.* 115:557–564 (1991). Furthermore, fluid-phase [$^{125}$I]P-selectin binds with high affinity to a limited number of sites on myeloid cells, whereas it binds with lower affinity to a higher number of sites on NeoLewis CHO cells. The 120,000 D glycoprotein ligand for P-selectin in neutrophil extracts is likely to correspond to the limited number of protease-sensitive, high affinity binding sites for P-selectin on intact neutrophils. Interaction of P-selectin with these sites may be required for efficient adhesion of leukocytes in flowing blood to P-selectin expressed by activated platelets or endothelial cells.

Further structural features of the glycoprotein ligand for P-selectin and a method for purifying the ligand are described below. The purified ligand, or fragments thereof (including both the carbohydrate and protein components), or antibodies to the ligand, or fragments thereof, can be used as inhibitors of binding of P-selectin to cells.

Materials and Methods

Materials

Wheat germ agglutinin (WGA)-agarose, pepstatin, aprotinin, N-acetylglucosamine, leupeptin, antipain, benzamidine, MOPS, Pipes, BSA, EDTA, EGTA, and Ponceau S were purchased from Sigma Chemical Co. (St. Louis, Mo.). Diisopropylfluorophosphate, dichloroisocoumarin, Triton X-100 (protein grade), and sialidase (neuraminidase) from *Arthrobacter ureafaciens* (75 U.mg, EC 3.2.1.18) were obtained from Calbiochem-Behring Corp. (La Jolla, Calif.), Micro BCA protein assay kits and Lubrol PX (Surfact Amp PX) were purchased from Pierce Chemical Company (Rockford, Ill.). Enzymobeads™, Tween-20, Affigel™-15, and high molecular weight protein standards were from Bio Rad Laboratories (Richmond, Calif.). Endo-β-galactosidase (150 U/mg, EC 3.2.1.103) from *Bacteroides fragilis*, 4-methyl-umbelliferyl α-N-acetylneuraminic acid, and 2,3- dehydro-2,3-dideoxy-N-acetylneuraminic acid (Neu2en5Ac) were obtained from Boehringer Mannheim Biochemicals (Indianapolis, Ind.). Peptide:N glycosidase F (PNGaseF) from *Flavobacterium meningosepticum* (EC 3.2.2.18, N-glycanase) and endo-α-N-acetylgalactosaminidase from *Diplococcus pneumoniae* (EC 3.2.1.97, O-glycanase™) were purchased from Genzyme (Cambridge, Mass.). HBSS was obtained from Gibco Laboratories (Grand Island, N.Y.). Vecta-Stain ABC kits were purchased from Vector Laboratories Inc. (Burlingame, Calif.). Phycoerythrin-streptavidin was obtained from Becton Dickinson & Co. (San Jose, Calif.) and phycoerythrin-conjugated anti-mouse $IgG_1$ was from Caltag (South San Francisco, Calif.). Rabbit anti-mouse IgG was purchased from Organon Teknika (Durham, N.C.) and protein A-Sepharose CL4B was from Pharmacia Fine Chemicals (Piscataway, N.J.). [6-$^3$H]glucosamine was obtained from Dupont/New England Nuclear (Boston, Mass.). All other chemicals were of the highest grade available.

Antibodies and Proteins

The anti-P-selectin murine mAbs S12 and G1, and goat anti-human P-selectin IgG were prepared and characterized as described by McEver and Martin, "A monoclonal antibody to a membrane glycoprotein binds only to activated platelets" *J. Biol. Chem.* 259:9799–9804 (1984); Geng et al., (1990); Lorant et al., (1991). Rabbit polyclonal antisera and murine mAbs to human lamp-1 (CD3), described by Carlsson et al., "Isolation and characterization of human lysosomal membrane glycoproteins, h-lamp-1 and h-lamp-2. Major sialoglycoproteins carrying polylactosaminoglycan" *J. Biol. Chem.* 263:18911–18919 (1988), and lamp-2 (BB6), Carlsson and Fukuda, "Structure of human lysosomal membrane glycoprotein 1. Assignment of disulfide bonds and visualization of its domain arrangment" *J. Biol. Chem.* 264:20526–20531 (1989), and rabbit polyclonal anti-human leukosialin antiserum, described by Carlsson and Fukuda, "Isolation and characterization of leukosialin, a major sialoglycoprotein on human leukocytes" *J. Biol. Chem.* 261:12779–12786 (1986) were provided by Dr. Sven Carlsson (University of Umea, Umea, Sweden). Anti-human leukosialin (CD43) mAb (Leu-22) was purchased from Becton Dickinson & Co. (San Jose, Calif.). The anti-L-selectin murine mAb antibodies DREG-56, DREG-55, and DREG-200, described by Kishimoto et al., "Identification of a human peripheral lymph node receptor: a rapidly down-regulated adhesion receptor" *Proc. Natl. Acad. Sci. USA* 87:2244–2248 (1990) were provided by Dr. Takashi Kei Kishimoto (Boehringer Ingelheim Pharmaceuticals, Inc., Ridgefield, Conn.). All mAbs are of the $IgG_1$ subtype and were used in purified form. Leukosialin purified from HL 60 cells (Carlsson and Fukuda, 1986) was provided by Dr. Sven Carlsson (University of Umea). P-selectin was purified from human platelets as described by Moore et al., (1991). The teachings of these references are specifically incorporated herein.

Preparation of Membranes

Erythrocyte membranes were isolated from leukocyte-depleted human erythrocytes as described by Rollins and Sims, "The-complement-inhibitory activity of CD59 resides in its ability to block incorporation of C9 into membrane C5b9" *J. Immunol.* 144:3478–3483 (1990) and extracted with 0.1 M NaCl, 10 mM MOPS, pH 7.5, 1% Lubrol™ PX. Detergent-insoluble material was removed by centrifugation at 16,000 g for 10 min.

Human neutrophils isolated by discontinuous leukopheresis from volunteer donors were purchased from the Oklahoma Blood Institute (Oklahoma City, Okla.). Each product contained $1.5–3.3\times10^{10}$ leukocytes (approximately 85% neutrophils). The neutrophil product was centrifuged at 200 g for 20 min and the platelet-rich plasma removed. Erythrocytes were lysed by resuspending the pellets with 5 mM EDTA, pH 7.5, in $H_2O$ for 20 s. An equal volume of 1.8% NaCl, 5 mM EDTA, pH 7.5, was then added to restore isotonicity. The cells were centrifuged at 500 g for 5 min and resuspended in ice-cold HBSS containing 5 mM EDTA and 10 mM MOPS, pH 7.5. Diisopropylfluorophosphate was then added to a final concentration of 2 mM and the cell suspension incubated for 10 min on ice. The cells were centrifuged at 500 g for 5 min at 4° C. and resuspended in ice-cold 100 mM KCl, 3 mM NaCl, 1 mM $Na_2ATP$, 3.5 mM $MgCl_2$, 10 mM Pipes, pH 7.3 (relaxation buffer). To this suspension the following protease inhibitors were added at the indicated final concentrations: 2 mM diisopropylfluorophosphate, 20 µM leupeptin, 30 µM antipain, and 1 mM benzamidine. The cell suspension was pressurized with $N_2$ at 350 psi in a cell disruption bomb (model 4635; Parr Instrument Company, Moline, Ill.) for 40 min at 4° C. with constant stirring as described by Borregaard et al., "Subcellular localization of the b cytochrome component of the human neutrophil microbiocidal oxidase: Translocation during activation" *J. Cell Biol.* 97:52–61 (1983). The cavitate was collected into EGTA (2 mM final concentration) and nuclei and undisrupted cells were pelleted at 500 g for 10 min at 4° C. The cavitate was fractionated as described by Eklund and Gabig, "Purification and characterization of a lipid thiobis ester from human neutrophil cytosol that reversibly deactivates the $O^2$-generating NADPH oxidase" *J. Biol. Chem.* 265:8426–8430 (1990). Briefly, it was layered over 40% sucrose in relaxation buffer containing 2 mM EGTA, 20 µM leupeptin, 30 µM antipain, and 1 mM benzamidine, and centrifuged at 104,000 g (at $r_{av}$) for 45 min at 4° C. in a rotor (model SW28; Beckman Instruments, Inc., Palo Alto, Calif.). The top layer ($FX_1$), the 40% sucrose layer ($FX_2$), and the granule pellet ($FX_3$) were collected and assayed for lactate dehydrogenase as a cytoplasmic marker, alkaline phosphatase as a plasma membrane marker, and myeloperoxidase as a marker for azurophilic granules as described by Borregaard et al., (1983); Geng et al., (1990).

Table I shows the distribution of marker enzymes in the various fractions. $FX_2$, enriched for alkaline phosphatase, was diluted with four volumes of 0.1 M NaCl, 10 mM MOPS, pH 7.5, and centrifuged at 111,000 g (at $r_{av}$) for 60 min at 4° C. in a rotor (model 50.2 Ti; Beckman Instruments, Inc.). The supernatant was collected and the membrane pellet was extracted with 1% Lubrol™ PX, 0.1 M NaCl, 10 mM MOPS, pH 7.5, 0.02% sodium azide, 20 µM leupeptin, 30 µM antipain, 1 mM benzamidine, and stored at 4° C.

HL-60 cells, maintained in suspension culture in RPMI-1640 supplemented with 10% FCS, 100 IU/ml penicillin, and 100 µg/ml streptomycin, were washed in HBSS, 10 mM MOPS, pH 7.5, and membranes were isolated exactly as described for neutrophils.

Partial Purification of P-selectin Ligand

Neutrophil or HL-60 cell membrane extracts were applied to a wheat germ agglutinin (WGA) affinity column (0.9×20 cm. 7.6 mg lectin/ml resin) equilibrated at room temperature with 0.5 M NaCl, 10 mM MOPS, pH 7.5, 0.02% sodium azide, 0.1% Lubrol™ PX. The column was washed with five column volumes of equilibration buffer, followed by two column volumes of 0.1 M NaCl, 10 mM MOPS, pH 7.5, 5 mM EDTA, 0.02% sodium azide, 0.01% Lubrol™ PX. The column was then eluted with the above buffer containing 100 mM N-acetylglucosamine. Protein-containing fractions were pooled and extensively dialyzed against 0.1 M NaCl, 10 mM MOPS, pH 7.5, 0.02% sodium azide, 0.01% Lubrol™ PX at 4° C. The dialyzed WGA column eluate was made 1 mM in $CaCl_2$ and $MgCl_2$ and applied to a human serum albumin Affigel™-15 precolumn (0.9×11 cm, 25 mg protein/ml resin) hooked in series to a P selectin-Affigel™-15-column (0.6×13 cm, 2 mg protein/ml resin). The columns were equilibrated with 0.1 M NaCl, 10 mM MOPS, pH 7.5, 1 mM $CaCl_2$, 1 mM $MgCl_2$, 0.02% sodium azide, 0.01% Lubrol™ PX. After the samples were applied the columns were washed with 100 column volumes of equilibration buffer, and eluted with equilibration buffer containing 5 mM EDTA. Yields were estimated by protein assays with the Micro BCA protein assay kit using BSA as a standard.

TABLE I

Distribution of Marker Enzymes from Subcellular Fractions of Nitrogen-cavitated Human Neutrophils.

| | Lactate dehydrogenase | Myeloperoxidase | Alkaline phosphatase |
|---|---|---|---|
| $FX_1$ (cytosol) | 95.6 ± 0.5 | 0 | 29.0 ± 2.7 |
| $FX_2$ (membrane) | 4.1 ± 0.5 | 2.6 ± 1.0 | 56.8 ± 8.7 |
| $FX_3$ (granule) | 0 | 97.4 ± 1.0 | 14.1 ± 5.5 |

Results are expressed as the percentage of the total enzyme activity in the cavitate (mean ± SD, n = 3).

P-selectin Blotting Assay

Samples were electrophoresed on 7.5% SDS polyacrylamide gels and proteins electrophoretically transferred to Immobilon-P™ membranes (Millipore Corp., Bedford, Mass.) for 4–5 h at 0.5 A. The positions of the molecular weight standards were marked with a pen after staining the membranes with Ponceau S. The membranes were blocked overnight at 4° C. in 0.1 M NaCl, 10 mM MOPS, pH 7.5, 1 mM $CaCl_2$, 1 mM $MgCl_2$, 0.02% sodium azide, 10% (wt/vol) Carnation™ nonfat dry milk, and then washed with the same buffer containing 0.1% Tween-20 without milk. The membranes were incubated with [$^{125}$I]P-selectin (0.5–1.0 nM), iodinated as described by Moore et al., 1991, using standard techniques, in 0.1 M NaCl, 10 mM MOPS, pH 7.5, 1 mM $CaCl_2$, 1 mM $MgCl_2$, 0.05% Lubrol™ PX, 1% human serum albumin for 1 h at room temperature. After extensive washing the membrane was dried and exposed to Kodak X-OMAT AR film (Eastman Kodak Company, Rochester, N.Y.) for 6 18 at −70° C. All the [$^{125}$I]P-selectin blots shown are autoradiograms of the entire blot, corresponding to the area from the stacking gel interface to beyond the dye front on the original gel.

P Metabolic Radiolabeling of HL-60 Cells and Isolation of [$^3$H]glucosamine-labeled P-selectin Ligand HL-60 cells (1–2×10$^6$ cells/ml) in 100-mm tissue culture dishes were labeled for 48 h with 50 μCi/ml [6-$^3$H] glucosamine at 37° C. in RPMI-1640 containing 10% FCS, 2 mM glutamine, 100 IU/ml penicillin, and 100 μg/ml streptomycin. At the end of the labeling periods the cells were washed three times by centrifugation and resuspension in ice-cold PBS. The cell pellet was solubilized with 0.1 M NaCl, 10 mM MOPS, pH 7.5, 4 mM $CaCl_2$, 4 mM $MgCl_2$, 1% Triton X-100, 20 μg/ml aprotinin, 20 μg/ml leupeptin, 8 μg/ml pepstatin, 2 mM PMSF, 10 mM benzamidine, and 0.5 mM dichloroisocoumarin. The solubilized cells were allowed to sit on ice for 1–2 h and then sonicated for 20 min at 4° C. in a water bath sonicator. The cell extract was centrifuged for 5 min at 16,000 g and the supernatant was applied to a P selectin-Affigel-15™-column (0.25×13 cm, 2 mg protein/ml resin) equilibrated with 0.1 M NaCl, 10 mM MOPS, pH 7.5, 2 mM $CaCl_2$, 2 mM $MgCl_2$, 0.1% Triton X 100. The column was washed with 10–20 column volumes of equilibration buffer and bound material was eluted with equilibration buffer containing 10 mM EDTA. Fractions (1 ml) were collected and monitored for radioactivity by liquid scintillation counting.

Analysis of [$^3$H]glucosamine-labeled P-selectin Ligand

Metabolically labeled proteins eluted from the P-selectin column were precipitated in the presence of 0.1 mg/ml BSA by addition of cold TCA (10% final concentration). The resulting pellets were washed with 1 ml acidified acetone (0.2%), solubilized in 0.1 M NaOH and electrophoresed under reducing and nonreducing conditions on 10% SDS-polyacrylamide gels. The gels were stained with Coomassie blue and then processed for fluorography with EN$^3$HANCE (Dupont/New England Nuclear, Boston, Mass.) according to the manufacturer's instructions. The dried gels were then exposed to Kodak X-OMAT AR film at −80° C.

Enzyme Digestion

In certain experiments, samples analyzed by P-selectin blotting were pretreated with exo- or endo-glycosidases before SDS-PAGE. For sialidase and endo-β-galactosidase digestions of P-selectin ligand, samples were dialyzed against 0.15 M NaCl, 50 mM acetate, pH 6.0, 9 mM $CaCl_2$, 0.02% azide, 0.01% Lubrol™ PX, and incubated for various times at 37° C. in the presence or absence of 200 mU/ml of enzyme. For PNGaseF and endo-α-N-acetylgalactosaminidase digestions, samples were first reduced and denatured by boiling in 0.5% SDS, 0.5% β-mercaptoethanol for 5 min, and then a 7.5-fold molar excess of NP-40 was added. The samples were incubated for 16 h at 37° C. with either PNGaseF (20 U/ml at pH 8.6) or endo-α-N acetylgalactosaminidase (70 mU/ml at pH 6.5) in the presence of 5 mM PMSF and 5 mM 1,10 phenanthroline.

Affinity purified [$^3$H]glucosamine-labeled P-selectin ligand was incubated for 24 h in 25 mM sodium acetate, pH 5.5 at 37° C. under a toluene atmosphere in the presence or absence of 1 U/ml of A. ureafaciens sialidase for 18 h. For PNGaseF digestion of metabolically labeled ligand, samples were denatured by boiling in 0.25% SDS, 25 mM β-mercaptoethanol for 5 min, and NP-40 was added in eight-fold excess (wt/wt) over SDS. The samples were incubated for 24 h with PNGaseF (3.3 U/ml) in a toluene atmosphere. The samples were then precipitated with TCA and subjected to SDS-PAGE and fluorography as described above.

Flow Cytometry

Human neutrophils, isolated as described by Hamburger and McEver, (1990), were suspended (10$^6$/ml) in HBSS containing 1% FCS and 0.1% sodium azide (HBSS/FCS/Az). 1 ml of neutrophil suspension was underlaid with 100 μl FCS and centrifuged at 500 g for 5 min. The neutrophil pellet was resuspended in 50 μl of purified P selectin (10 μl/ml, in HBSS/FCS/Az), and then incubated sequentially with 50 μl of biotin-conjugated S12 (10 μg/ml, in HBSS/FCS/Az) and 20 μl of phycoerythrin-streptavidin (neat). In certain experiments, the neutrophils were preincubated for 10–15 min with antisera or antibodies before the addition of P-selectin. Between each step the cells were diluted with one ml of HBSS/FCS/Az, underlaid with 100 μl FCS, and centrifuged at 500 g for 5 min. All steps were performed at 4° C. After the last wash, the cells were fixed with 1 ml of 1% paraformaldehyde in HBSS and analyzed in a FACScan flow cytometer (FACScan is a registered trademark of Becton Dickinson & Co., Mountain View, Calif.) formatted for two color analysis as described by Moore, et al., (1991). Binding of P-selectin to intact neutrophils as assessed by this assay was $Ca^{2+}$-dependent, was blocked by G1, and was abolished by pretreatment of the cells with trypsin or sialidase.

Immunoprecipitations

WGA eluate was incubated with 10 µg of anti-leukosialin (Leu22) or an isotype matched control monoclonal antibody for 1 h at 37° C. The mixture was then incubated with protein A-Sepharose CL4B beads saturated with rabbit anti-mouse IgG for 1 h at 37° C. The beads were pelleted, washed four times with 1 ml of 0.1 M NaCl, 20 mM Tris, pH 7.5, 1% Triton X-100, and bound material eluted by boiling 5 min in 2% SDS, 60 mM Tris, pH 6.8, and 5% β-mercaptoethanol. Immunoprecipitates and immunosupernatants were then analyzed by P-selectin blotting and by Western blotting using Leu22 as a probe.

Assay of Sialidase Activity in Commercial Enzyme Preparations

The sialidase activity in O-glycanase (endo-α N-acetylgalactosaminidase) or *A. ureafaciens* sialidase was assayed by incubation of dilutions of the enzymes with 50 nmol 4-methyl-umbelliferyl-α-N-acetylneuraminic acid in 50 µl of sodium cacodylate, pH 6.5, 10 mM calcium acetate, for various time periods. Incubations were quenched by addition of 0.95 ml 0.1 M sodium bicarbonate, pH 9.3, and assayed for released 4-methylumbelliferone by fluorescence (excitation=365 nM, emission=450 nM).

Results

Identification of a P-selectin Ligand

To identify proteins from myeloid cells which bind P-selectin, neutrophil and HL-60 cell membrane extracts were electrophoresed on 7.5% SDS-polyacrylamide gels, transferred to Immobilon membranes, and probed with [$^{125}$I] P-selectin. When samples were analyzed without reduction, P-selectin bound preferentially to a glycoprotein species with an approximately 250,000 $M_r$ from both neutrophil and HL-60 cell membranes as determined by SDS-PAGE. Cell membrane extracts (80 µg protein/lane) were electrophoresed on 7.5% SDS-polyacrylamide gels under nonreducing or reducing conditions, transferred to Immobilon membranes, and probed with [$^{125}$I]P-selectin. Under nonreducing conditions P-selectin also bound to proteins at the stacking gel interface and to a minor species with an approximately 160,000 $M_r$. When samples were analyzed after reduction, P-selectin preferentially bound to a glycoprotein with an approximately 120,000 $M_r$. Minor bands were observed at approximately 250,000 and approximately 90,000 $M_r$. Under both reducing and nonreducing conditions P-selectin also bound to the blots at the dye front. P-selectin binding proteins were not detected when an equivalent amount of erythrocyte membrane protein was analyzed in parallel. The total proteins in the neutrophil cavitate were also solubilized with SDS and analyzed for their ability to interact with P-selectin with the blotting assay. P-selectin bound only to proteins with apparent molecular weights of 120,000 and 90,000 under reducing conditions. Although the sensitivity of this analysis was limited by the amount of protein that could be run on the gel, the results indicate that we did not exclude major ligands that were either not enriched in the membrane fraction ($FX_2$) or not effectively solubilized by nonionic detergent.

To further assess the specificity of the blotting assay, neutrophil membrane extracts electrophoresed under reducing conditions were probed with [$^{125}$I]P-selectin in the presence or absence of EDTA or anti-P-selectin mAbs. Neutrophil membrane extracts (200 µg protein/lane) were electrophoresed on 7.5% SDS-polyacrylamide gels under reducing conditions, transferred to Immobilon membranes, and probed with [125I]P-selectin alone, in the presence of 10 mM EDTA, or in the presence of 20 µg/ml of the anti-P selectin mAbs G1 or S12. [$^{125}$I]P-selectin binding to the major 120-kD and the minor 250-kD species was $Ca^{2+}$-dependent, a characteristic of all selectin-dependent cellular interactions. Binding to both species was also blocked by G1, a mAb to P-selectin that inhibits adhesion of myeloid cells to P-selectin, but not by S12, a mAb to P-selectin that does not block adhesion. Binding of [$^{125}$I]P-selectin was also inhibited by a 100-fold excess of unlabeled P-selectin. The binding of [$^{125}$I]P-selectin to the dye front and to the 90,000 D protein was not blocked by EDTA or G1, suggesting that these interactions were nonspecific or used a specific $Ca^{2+}$-independent recognition mechanism.

Purification of P-selectin Ligand from neutrophils

Neutrophils were disrupted and the membrane fraction ($FX_2$) isolated by fractionation of the cavitate as described in Materials and Methods. The membrane fraction constituted approximately 5–7% (n>10) of the protein in the cavitate. This fractionation depleted both cytosolic proteins and azurophilic granules (Table I). Proteins binding P-selectin were not detected in the cytosolic fraction ($FX_1$) with the blotting assay. The final membrane pellet was solubilized with nonionic detergent and applied to a WGA column which bound 4–5% of the protein in the membrane extract. P-selectin blotting assays of reduced proteins demonstrated that both the major 120,000 D and the minor 250,000 D ligands bound quantitatively to WGA. However, the 90,000 D band and the band at the dye front observed in the membrane extract were not bound by WGA. After extensive dialysis, the WGA eluate was applied to an Affigel-15™ precolumn in series with a P-selectin affinity column. Approximately 2% of the protein in the WGA eluate bound to the P-selectin column and could be eluted with EDTA. Both the 250,000 D and the 120,000 D ligands bound quantitatively to the P-selectin column. Quantitative analysis of the protein recovered from the P-selectin eluate indicated that the ligand(s) formed less than 0.01% of the total protein in the neutrophil cavitate. Elution of bound proteins from the P-selectin column with EDTA demonstrated that the interaction of nondenatured neutrophil ligands with P-selectin was also $Ca^{2+}$-dependent. Neither species was eluted from the Affigel-15 precolumn with EDTA.

A silver-stained SDS-polyacrylamide gel of proteins from the various stages in the partial purification procedure was run under reducing conditions. Samples from the indicated steps of the isolation procedure were electrophoresed on 7.5% SDS-polyacrylamide gels under reducing conditions, transferred to Immobilon membranes, and probed with [$^{125}$I] P-selectin. The amounts of protein loaded onto the lanes were as follows: membrane extract and WGA flow through, 200 µg; WGA eluate and P-selectin flow through, 50 µg; P-selectin eluate, 2 µg. The same samples (10 µg protein/lane) were also analyzed by SDS-PAGE under the reducing conditions followed by silver staining. The major silver-stained band in the P-selectin eluate had an approximately 150,000 $M_r$ which is similar to that of P-selectin itself. To determine whether this protein represented P-selectin that had leached off the P-selectin column, the P-selectin eluate was analyzed by SDS-PAGE under both reducing and non-reducing conditions, followed by silver staining, Western blotting with goat anti-P-selectin IgG, and P-selectin blotting. The major silver-stained protein in the P-selectin eluate was indeed P-selectin. Purified P-selectin migrates with an approximately 120,000 $M_r$ under nonreducing conditions; a minor component migrates with an approximately 250,000 $M_r$. After reduction the protein migrates more slowly with an approximately 150,000 $M_r$. The two nonreduced bands and the one reduced band detected by silver staining of the P-selectin eluate co-migrated with purified P-selectin and were recognized by anti-P-selectin IgG. The P-selectin ligand identified in the blotting assay was not detected by silver staining and migrated differently than P-selectin under both reducing and nonreducing conditions. When the P-selectin eluate was electrophoresed without reduction, P-selectin did not bind to proteins at the stacking gel interface. Therefore, the P-selectin binding proteins at the stacking gel interface, observed in extracts of neutrophil membranes, were probably an artifact due to the relatively high amount of protein loaded on the gel.

Characterization of the P-selectin Ligand

The ligand(s) on intact target cells requires sialic acids to interact with P-selectin. To determine whether the ligand detected by blotting of neutrophil membranes contained sialic acids that were essential for recognition by P-selectin, neutrophil membrane glycoproteins which bound to WGA were treated with sialidase (200 mU/ml) for varying times before SDS-PAGE under reducing conditions and then analyzed for their ability to bind P-selectin. Neutrophil WGA eluate (50 µg) was either sham-treated or digested with 200 mU/ml of sialidase or with 20 U/ml of PNGaseF for 16 h, then electrophoresed on 7.5% SDS polyacrylamide gels under reducing conditions, transferred to Immobilon membranes, and probed with [$^{125}$I]P-selectin.

Sialidase digestion for 30 min increased the apparent molecular weight of the major 120,000 D ligand, a shift characteristic of heavily sialylated glycoproteins. Longer sialidase digestion did not further alter the electrophoretic mobility of the ligand but did abolish its ability to bind [$^{125}$I]P-selectin. Sialidase treatment had a similar effect on the minor 250 kD ligand.

These results demonstrate that the ligand(s) contains sialic acid residues that are critical for recognition by P-selectin, but suggest that only a portion of the sialic acid residues are required for binding.

To examine whether the ligand contained N-linked glycans, neutrophil membrane glycoproteins which bound to WGA were digested with PNGaseF. This treatment did not affect [$^{125}$I]P-selectin binding but did decrease the apparent molecular weight of the ligand, consistent with the enzymatic removal of one or two N-linked glycan chains. This demonstrates that the ligand contains at least one N-linked oligosaccharide chain that is not required for P-selectin binding. Although one could not directly assess whether N-linked glycans were quantitatively removed from the ligand, conditions that normally cleave such glycans from most proteins were used.

Prolonged treatment of neutrophil membrane extracts with endo-α-N-acetylgalactosaminidase (O-glycanase) abolished binding of [$^{125}$I]P-selectin in the blotting assay, whereas sham digestion was without effect. This was a surprising result, since only nonsialylated Galβ1-3GalNAc disaccharides O-linked to serine or threonine residues are known substrates for the enzyme. Assays using a synthetic sialidase substrate confirmed the presence of a small amount of sialidase (0.01 mU/mU O-glycanase) contaminating the O-glycanase. Although the level of activity was small, it was stable to prolonged incubations under the conditions recommended by the manufacturer for use of the O-glycanase preparation. To prove that the contaminating sialidase was responsible for the loss of P-selectin binding, the digestions were repeated in the presence of a competitive sialidase inhibitor, Neu2en5Ac. Under these conditions endo-α-N-acetylgalactosaminidase digestion had no effect on [$^{125}$I]P-selectin binding to the ligand or the apparent molecular weight of the ligand. Because the ligand requires sialic acid to interact with P-selectin, the blotting assay could not be used to assess the role of O-linked glycans in recognition by P-selectin.

P Isolation of a P-selectin Ligand from Metabolically Labeled HL-60 Cells

P-selectin blotting of denatured membrane proteins from myeloid cells may not detect molecules whose ability to bind P-selectin is dependent on secondary and/or tertiary structure. As an independent approach to identify ligands for P-selectin, HL-60 cells were metabolically labeled with [$^3$H]glucosamine, solubilized with nonionic detergent, and applied to a P-selectin affinity column. After extensive washing, bound material was eluted with EDTA and analyzed by SDS-PAGE followed by fluorography. Samples were electrophoresed on 10% SDS polyacrylamide gels under both nonreducing and reducing conditions and analyzed by fluorography. Other samples were either sham treated or digested with 1 U/ml of sialidase for 24 h or with 3.3 U/ml of PNGaseF for 24 h, and then electrophoresed on 10% SDS polyacrylamide gels under reducing conditions and analyzed by fluorography.

A single metabolically labeled species was eluted, which co-migrated under both nonreducing and reducing conditions with the major species detected in neutrophil and HL-60 cell membranes by blotting with [$^{125}$I]P-selectin. Only 0.15–0.5% of the total [$^3$H]glucosamine-labeled HL-60 glycoproteins bound to the P-selectin column, indicating that the ligand is not abundant. Sialidase treatment of the [$^3$H]glucosamine-labeled P selectin ligand from HL-60 cells produced the same increase in apparent molecular weight that was observed for the major neutrophil ligand identified by the P-selectin blotting assay. In addition, PNGaseF treatment caused the same decrease in the apparent molecular weight of the HL-60 cell ligand that was observed for the neutrophil ligand.

Comparison of the P-selectin Ligand with Known Neutrophil Membrane Proteins

The properties of the major 120,000 D P-selectin ligand were compared with those of three well-characterized neutrophil membrane proteins with similar apparent molecular weight. The first two molecules, lamp-1 and lamp-2, are abundant neutrophil proteins that are predominantly localized in lysosomal membranes but are also expressed in small amounts on the cell surface. These proteins have a large number of complex N-linked glycan chains, many of which carry the sialyl Le$^x$ tetrasaccharide. Polyclonal antisera (1:5 dilution) and mAbs (40 µg/ml) to lamp-1 (CD3) and lamp-2 (BB6) had no effect on binding of P-selectin to neutrophils as assessed by flow cytometry.

Membrane extracts (200 µg protein/lane) were electrophoresed on 7.5% SDS-polyacrylamide gels under nonreducing or reducing conditions, transferred to Immobilon membranes, and probed with [$^{125}$I]P-selectin or murine monoclonal antibodies directed against human lamp-1 (CR3), human lamp-2 (BB6), human L-selectin (DREG-200), or human leukosialin (Leu22). Western blot analysis of neutrophil membranes with mAbs to lamp-1 and lamp-2 showed that the electrophoretic mobilities of these proteins under nonreducing conditions were distinct from that of the P-selectin ligand. In contrast to the P-selectin ligand, the electrophoretic mobilities of lamp-1 and lamp-2 are not affected by sialidase treatment. Although lamp-1 and lamp-2 from myeloid cells are rich in lactosaminoglycans sensitive to endo-β-galactosidase, treatment of intact neutrophils with the enzyme did not affect binding of [$^{125}$I]P-selectin. Pretreatment of crude neutrophil membrane extracts or WGA column eluate with endo β-galactosidase (200 mU/ml, 1–2 h, 37° C.) also did not affect the apparent molecular weight of the ligand or its ability to bind [$^{125}$I]P-selectin. These data argue that lamp-1 and lamp-2 are not ligands for P-selectin even though they carry many sialyl Le$^x$ structures.

The third molecule whose apparent molecular weight is similar to the 120,000 D P-selectin ligand is CD43 (leukosialin, sialophorin), a heavily sialylated membrane protein present on platelets and all leukocytes. It carries numerous O-linked sugar chains and is differentially glycosylated by cells of various hematopoietic lineages. Like the P-selectin ligand, treatment of leukosialin with sialidase increases its apparent molecular weight. However, in contrast to the P-selectin ligand, the electrophoretic mobility of leukosialin was unaffected by reduction. Monospecific polyclonal anti-human leukosialin antisera (1:5 dilution) did not inhibit P-selectin binding to neutrophils as assessed by flow cytometry. Furthermore, immunodepletion of leukosialin from neutrophil membrane extracts did not deplete P-selectin ligand as assessed by the blotting assay. Finally, leukosialin purified from HL-60 cells did not bind P-selectin. Neutrophil WGA eluate (50 μg) and leukosialin purified from HL-60 cells (0.5 μg) were electrophoresed under reducing conditions on 7.5% SDS-polyacrylamide gels, transferred to Immobilon, and probed with [$^{125}$I]P-selectin. The same membrane was then probed with the monoclonal anti-human leukosialin antibody Leu22.

Based on studies in which an antibody to L-selectin (DREG-56) partially inhibited neutrophil adhesion to P-selectin-transfected cells, it was suggested that L-selectin is an important glycoprotein ligand on myeloid cells for P-selectin by Picker et al., "The neutrophil selectin LECAM-1 presents carbohydrate ligands to the vascular selectins ELAM-1 and GMP-140" *Cell* 66:921–933 (1991). Although L-selectin is present in membrane extracts and WGA eluates of neutrophil membranes, as detected by Western blotting, [$^{125}$I]P-selectin did not bind to L-selectin in the blotting assay. In addition, the anti-L-selectin mAb DREG-56 (100 μg/ml) had no effect on the binding of purified P-selectin to quiescent neutrophils as assessed by flow cytometry. Neutrophils were preincubated for 15 min with buffer alone, 100 μg/ml of the anti-L-selectin monoclonal antibody DREG-56, or 100 μg/ml of the anti-P-selectin mAb G1 before addition of buffer or P-selectin. P-selectin binding was then detected by sequential incubation of the cells with biotinylated S12 (a noninhibitory monoclonal antibody to P-selectin) and phycoerythrin-streptavidin as described in Materials and Methods.

Parallel control assays showed that the neutrophils expressed high levels of L-selectin detectable by DREG-56. Binding of the anti-L-selectin mAb DREG-56 to the neutrophils was assessed by indirect immunofluorescence using a phycoerythrin-conjugated anti-murine IgG$_1$ antibody. Identical results were obtained with the anti-L-selectin mAbs DREG-55 and DREG-200. Thus, interactions with L-selectin do not appear to contribute to the binding of fluid-phase P-selectin to intact neutrophils or to immobilized proteins from neutrophil membrane extracts.

The following additional observations have been made relating to the ligand.

Treatment of the $^3$H-glucosamine-labeled P-selectin ligand from HL-60 cells with neuraminidase releases approximately 30% of the radioactivity as sialic acid.

Strong acid hydrolysis of the $^3$H-glucosamine-labeled P-selectin ligand from HL-60 cells releases both $^3$H-glucosamine and $^3$H-galactosamine in the approximate ratio of 2:1, indicating that the ligand contains both N-acetylglucosamine and N-acetylgalactosamine. In most glycoproteins structurally defined to date, the glucosamine and galactosamine occur as the acetylated derivatives.

The presence of N-acetylgalactosamine is indicative of the presence of O-linked oligosaccharides (or Ser/Thr-linked oligosaccharides) in which GalNAc is commonly found in O-glycosidic α-linkage directly to amino acid. The indicated presence of O-linked oligosaccharide is confirmed by the further observation that the ligand binds quantitatively to the Jacalin-Sepharose, an immobilized plant lectin that binds to the core disaccharide sequence Galβ1-3GalNAcα-Ser/Thr in glycoproteins. Jacalin-Sepharose can bind to O-linked oligosaccharides that have modifications of this simple core. Thus, these results are not in conflict with the lack of sensitivity of the ligand to O-glycanase. When the $^3$H-glucosamine-labeled P-selectin ligand from HL-60 cells is treated with mild base in the presence of sodium borohydride (50 mM NaOH, 1 M NaBH$_4$, 16 hr at 45° C.) to cause a beta-elimination reaction, approximately two-thirds of the radioactivity is released as a moderately sized oligosaccharide with more than four sugar residues, as defined by chromatography on a column of BioGel P-10 in bicarbonate buffer. It is well known from previous published studies that oligosaccharides in O-glycosidic linkage, but not in N-glycosidic linkage, are susceptible to release from peptide by this treatment. These results further support the observation that the ligand contains a considerable amount of O-linked oligosaccharides.

Treatment of the $^3$H-glucosamine-labeled P-selectin ligand from HL-60 cells with O-glycanase and neuraminidase does not demonstrably affect the apparent mobility of the ligand any more than neuraminidase alone. This indicates that the ligand does not contain large amounts of the simple oligosaccharides in O-linkage to Ser/Thr residues. O-glycanase is an endoglycosidase which cleaves the sequence Galβ1-3GalNAcα-Ser/Thr in glycoproteins to release the disaccharide Galβ1-3GalNAc. Treatment of the $^3$H-glucosamine-labeled P-selectin ligand from HL-60 cells with neuraminidase causes a decrease in the electrophoretic mobility of the ligand.

The presence of numerous O-linked oligosaccharides on the ligand is confirmed by the sensitivity of the $^3$H-glucosamine-labeled P-selectin ligand from HL-60 cells to an enzyme termed O-glycoprotease. This enzyme is a protease which recognizes and cleaves peptide bonds within glycoproteins that contain numerous sialic acid-containing O-linked oligosaccharides.

The ligand contains the sialyl Lewis x (SLe$^x$) antigen (NeuAcα2-3Galβ1-4[Fucα1-3]GlcNAcβ-R). When the $^3$H-glucosamine-labeled P-selectin ligand from HL-60 cells was reapplied to a column of P-selectin-Affigel™ it rebound. When this chromatography was done in the presence of antibody to the SLe$^x$ antigen (CSLEX1 monoclonal antibody (Fukushima, et al., *Cancer Res.* 44:5279–5285, 1984), purchased from Dr. Paul Teraski, University of California at Los Angeles, binding was more than 90% reduced. In contrast, when a control experiment was done in which the rechromatography occurred in the presence of antibody to the Le$^x$ antigen (which lacks sialic acid), there was little if any effect. The CSLEX1 anti-SLe$^x$ antibody bound to the ligand as assessed by Western blotting.

The ligand contains poly-N-acetyllactosamine sequences of the type [3Galβ1-4GlcNAcβ1]$_n$. The $^3$H-glucosamine-labeled P-selectin ligand from HL-60 cells quantitatively binds to a column of immobilized tomato lectin, a plant lectin which has been shown to bind to poly-N-acetyllactosamine sequences within glycoproteins.

The ligand from HL-60 cells contains fucose. When HL-60 cells are incubated with 6-$^3$H-fucose, the P-selectin ligand is radioactively labeled. All incorporated radioactivity is in fucose. Furthermore, when the $^3$H-fucose-labeled ligand is treated with mild base and sodium borohydride to effect beta-elimination, $^3$H-fucose-labeled oligosaccharides are released that are both high molecular weight and moderate molecular weight, as estimated by chromatography on a column of BioGel P-10.

The differential mobility of the major ligand during SDS-PAGE in the presence and absence of reducing agents suggests that the native ligand is a disulfide-linked homodimer or that a 120,000 D subunit is disulfide linked to a distinct subunit that is not directly involved in P-selectin binding. Since only a 120,000 D band was detected after electrophoresis of reduced P-selectin eluate from metabolically labeled HL-60 cells, a heterodimer would have to consist of nonidentical subunits with the same apparent molecular weight and which undergo the same change in electrophoretic mobility after sialidase and PNGaseF digestion. Alternatively, the 120-kD-labeled subunit would have to be disulfide-linked to a subunit of similar apparent molecular weight that is not labeled with [$^3$H]glucosamine. A homodimeric ligand with two equivalent binding sites might enhance the avidity of the interaction with P-selectin. The ability of [$^{125}$I]P-selectin to bind to the ligand after reduction and denaturation with SDS suggests that higher order structural features of the protein are not critical for recognition.

The blotting assay also detected two minor ligands. The first has an approximately 250,000 M$_r$ under reducing conditions. Because its mobility is identical to that of the major ligand under nonreducing conditions, it may represent a subpopulation of the major ligand that is resistant to reduction. The second has an approximately 160,000 M$_r$ under nonreducing conditions. Binding of P-selectin to both minor ligands was Ca$^{2+}$ dependent and blocked by the mAb G1.

The isolation of a single glycoprotein from metabolically labeled HL-60 cells suggests that P-selectin has a marked preference for a particular ligand structure. L-selectin, which is expressed on leukocytes and binds to sialylated structures on endothelial cells, interacts preferentially with 50,000 D and 90,000 D sulfated, fucosylated glycoproteins from murine peripheral lymph nodes (Imai, et al., *J. Cell Biol.* 113:1213–1222, 1991). Thus, both P-selectin and L-selectin appear to interact with a small subset of glycoprotein ligands.

It has been demonstrated that L-selectin on neutrophils carries the sialyl Le$^x$ epitope and that a mAb to L-selectin partially blocks neutrophil adhesion to cells transfected with P-selectin cDNA (Picker, et al., *Cell* 66:921–933, 1991). Based on these observations, it was proposed that L-selectin on neutrophils is a predominant ligand for P-selectin. However, no direct interaction of L-selectin with P-selectin was demonstrated. In the present study, binding of P-selectin to L-selectin in neutrophil membrane extracts was not detectable. Furthermore, the binding of P-selectin to intact neutrophils is unaltered by antibodies to L-selectin or by neutrophil activation that causes shedding of L-selectin from the cell surface. Although it is conceivable that L-selectin has weak affinity for P-selectin, the significance of this potential interaction remains to be established.

A recombinant P-selectin IgG chimera was shown to bind to myeloid cells and to a sulfatide, Gal(3-SO$_4$) β1-Ceramide by Aruffo et al., "CD62/P-selectin recognition of myeloid and tumor cell sulfatides" *Cell* 67:35–44 (1991). Sulfatide also inhibited interaction of the chimera with monocytoid U937 cells, as reported by Aruffo et al., (1991). It was not demonstrated whether binding of the P-selectin chimera to the cells or to sulfatide was Ca$^{2+}$ dependent, a fundamental characteristic of selectin-dependent cellular interactions. Protease digestion of intact cells should increase the accessibility of P-selectin to potential glycolipid ligands such as sulfatides. However, protease treatment abolishes binding of P-selectin to neutrophils and HL-60 cells as well as adhesion of neutrophils to immobilized P-selectin. In addition, although erythrocytes and platelets express sulfatides, they do not specifically interact with P-selectin. Thus, it seems unlikely that sulfatides are the principal mediators of adhesion of myeloid cells to P-selectin. It remains to be determined whether sulfatides inhibit binding of P-selectin to myeloid cells by specific competition with a glycoprotein ligand or by indirect effects. It is possible that the P-selectin ligand described herein is sulfated or contains other structural features that are mimicked by sulfatides.

Previous studies by Zhou et al., (1991); and Polley et al., (1991) have shown that P-selectin interacts with α(2–3) sialylated, α(1–3)fucosylated lactosaminoglycans, of which one is the sialyl Le$^x$ tetrasaccharide. However, several observations suggest that the sialyl Le$^x$ tetrasaccharide per se does not bind with high affinity to P-selectin. First, some investigators (Moore et al., 1991; Aruffo et al., 1991; Polley, et al.), but not all, have found that sialyl Le$^x$ inhibits interactions of myeloid cells with P-selectin. Second, CHO cells transfected with a fucosyltransferase express sialyl Le$^x$ yet bind P-selectin with significantly lower affinity than do myeloid cells (Zhou et al., 1991). Third, HT-29 cells, which also express sialyl Le$^x$, do not interact at all with P-selectin (Zhou et al., 1991). Finally, several neutrophil membrane proteins known to carry the sialyl Le$^x$ structure, are distinct from the major glycoprotein ligand identified herein and do not bind P-selectin in the assays described here. These observations suggest that the ligand contains structural features in addition to the sialyl Le$^x$ tetrasaccharide that enhance the affinity and/or specificity of its interaction with P-selectin.

A blotting assay of neutrophil and HL-60 cell membrane extracts was used to search for ligands for P-selectin. As described previously in U.S. Ser. No. 07/650,484, [$^{125}$I]P-selectin bound preferentially to a glycoprotein of Mr 120,000 as assessed by SDS-PAGE under reducing conditions. Under nonreducing conditions, the ligand for P-selectin had an apparent Mr of 250,000, suggesting that it is a disulfide-linked homodimer. In initial studies, the ligand was partially purified by serial affinity chromatography on wheat germ agglutinin (WGA) and P-selectin affinity columns. Proteins bound to the P-selectin column were eluted with EDTA. The glycoprotein ligand was greatly enriched in the EDTA eluate from the P-selectin column, as assessed by the intensity of the band identified by [$^{125}$I]P-selectin blotting. As noted in U.S. Ser. No. 07/650,484, however, the ligand stained poorly with silver, consistent with its being an unusually heavily glycosylated protein. In the initial purifications, the only contaminating protein present noted by silver staining of the gel was a small amount of P-selectin itself which had been leached from the affinity column. Using a new P-selectin affinity column and more extensive washing procedures documented in the methods, the ligand has now been isolated free from contaminants. This conclusion is based on observation that there are no silver staining bands present but the ligand is clearly identified by its ability to interact with [$^{125}$I]P-selectin in the blotting assay.

As described in U.S. Ser. No. 07/650,484, partial removal of sialic acids with sialidase slowed the mobility of the ligand, a feature characteristic of heavily sialylated glycoproteins. Extensive sialidase digestion abolished recognition of the ligand by P-selectin. It has now been demonstrated that the ligand contain both N- and O-linked oligosaccharides.

A form of the ligand in which the carbohydrate components are radiolabeled has also been purified by P-selectin affinity chromatography, as described above. SDS-PAGE analysis of the P-selectin column eluate, followed by fluorography, indicates that the only labeled protein has an Mr of 250,000 under nonreducing conditions and 120,000 under reducing conditions. The radiolabeled ligand has the same shifts in electrophoretic mobility following treatment with sialidase or PNGase F. Thus, all the features of the radiolabeled ligand correspond to those of the ligand identified by the P-selectin blotting assay. Because only a single radiolabeled species is isolated from the P-selectin affinity column, the carbohydrate structures of the ligand can be analyzed in detail by procedures that have been developed, for example, as reported by R. D. Cummings and S. Kornfeld, *J. Biol. chem.* 257:11235–11240 (1982) and R. D. Cummings, et al., *J. Biol. Chem.* 258:15261–15273 (1983).

In summary, the glycoprotein ligand for P-selectin from myeloid cells has the characteristics of a disulfide-linked homodimer with each subunit having an apparent Mr of 120,000 as assessed by SDS-PAGE. The protein has some N-linked carbohydrate but its most striking feature is the presence of a large number of clustered O-linked glycans, most of which appear to be larger than the usual simple O-linked chains cleaved by O-glycanase. Although the ligand contains the sLe$^x$ structure, the data indicate that additional structural features in the ligand are required to confer high affinity binding to P-selectin. These features may include, but are not limited to, carbohydrate structures of more complexity than sLe$^x$ itself, clustering of many glycan chains to increase avidity, and specific orientations of the glycans relative to the protein backbone.

Preparation of Diagnostic and Therapeutic Agents Derived from the Protein or Carbohydrate Components of the Glycoprotein Ligand for P-selectin The glycoprotein ligand for P-selectin described above has a variety of applications as diagnostic reagents and, potentially, in the treatment of numerous inflammatory and thrombotic disorders.

Diagnostic Reagents

Antibodies to the ligand can be used for the detection of human disorders in which P-selectin ligands might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, immunoperoxidase or immunogold analysis, or other methods known to those skilled in the arts.

Antibodies directed specifically to protein or carbohydrate components of the ligand can be used to distinguish defects in expression of the core protein or in glycosyltransferases and/or modifying enzymes that construct the proper oligosaccharide chains on the protein. The antibodies can also be used to screen cells and tissues other than leukocytes for expression of the protein or carbohydrate components of the ligand for P-selectin.

Complementary DNA clones encoding the protein component of the ligand can be isolated and sequenced. These probes can be used as diagnostic reagents to examine expression of RNA transcripts for the ligand in leukocytes and other tissues by standard procedures such as Northern blotting of RNA isolated from cells and in situ hybridization of tissue sections.

A similar approach can be used to determine qualitative or quantitative disorders of P-selectin itself. The glycoprotein ligand, carbohydrates, or appropriate derivatives thereof, is labeled and tested for its ability to bind to P-selectin on activated platelets from patients with disorders in which P-selectin might be defective.

The ligand, or components thereof, can also be used in assays of P-selectin binding to screen for compounds that block interactions of P-selectin with the ligand.

Clinical Applications

Since P-selectin has several functions related to leukocyte adherence, inflammation, tumor metastases, and coagulation, clinically, compounds which interfere with binding of P-selectin and/or the other selectins, including E-selectin and L-selectin, such as the carbohydrates, can be used to modulate these responses. These compounds include the P-selectin ligand, antibodies to the ligand, and fragments thereof. For example, the glycoprotein ligand, or components thereof, particularly the carbohydrate moieties, can be used to inhibit leukocyte adhesion by competitively binding to P-selectin expressed on the surface of activated platelets or endothelial cells. Similarly, antibodies to the ligand can be used to block cell adhesion mediated by P-selectin by competitively binding to the P-selectin ligand on leukocytes or other cells. These therapies are useful in acute situations where effective, but transient, inhibition of leukocyte-mediated inflammation is desirable. In addition, treatment of chronic disorders may be attained by sustained administration of agents, for example, by subcutaneous or oral administration.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium- is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. Specifically, certain carcinoma cells have been demonstrated to bind to both E-selectin, as reported by Rice and Bevilacqua. *Science* 246:1303–1306 (1991), and P-selectin, as reported by Aruffo, et al., *Proc. Natl. Acad. Sci. USA* 89:2292–2296 (1992). The association of platelets with metastasizing tumor cells has been well described, suggesting a role for platelets in the spread of some cancers. Since P-selectin is expressed on activated platelets, it is believed to be involved in association of platelets with at least some malignant tumors.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

In these clinical applications, the glycoprotein ligand, or fragments thereof, can be administered to block selectin-dependent interactions by binding competitively to P-selectin expressed on activated cells. In particular, carbohydrate components of the ligand, which play a key role in recognition by P-selectin, can be administered. Similarly, natural or synthetic analogs of the ligand or its fragments which bind to P-selectin can also be administered. In addition, antibodies to the protein and/or carbohydrate components of the ligand, or fragments thereof, can be administered. The antibodies are preferrably of human origin or modified to delete those portions most likely to cause an immunogenic reaction. Carbohydrate components of the ligand or the antibodies, in an appropriate pharmaceutical carrier, are preferably administered intravenously where immediate relief is required. The carbohydrate(s) can also be administered intramuscularly, intraperitoneally, subcutaneously, orally, as the carbohydrate, conjugated to a carrier molecule, or in a drug delivery device. The carbohydrate can be modified chemically to increase its in vivo half-life.

The carbohydrate can be isolated from cells expressing the carbohydrate, either naturally or as a result of genetic engineering as described in the transfected COS cell examples, or, preferably, by synthetic means. These methods are known to those skilled in the art. In addition, a large number of glycosyltransferases have been cloned (J. C. Paulson and K. J. Colley, *J. Biol. Chem.* 264:17615–17618, 1989). Accordingly, workers skilled in the art can use a combination of synthetic chemistry and enzymatic synthesis to make pharmaceuticals or diagnostic reagents.

Protein fragments of the ligand can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Carbohydrates that are biologically active are those which inhibit binding of leukocytes to P-selectin. Suitable pharmaceutical vehicles for administration to a patient are known to those skilled in the art. For parenteral administration, the carbohydrate will usually be dissolved or suspended in sterile water or saline. For enteral administration, the carbohydrate will be incorporated into an inert carrier in tablet, liquid, or capsular form. Suitable carriers may be starches or sugars and include lubricants, flavorings, binders, and other materials of the same nature. The carbohydrate can also be administered locally at a wound or inflammatory site by topical application of a solution or cream.

Alternatively, the carbohydrate may be administered in, on or as part of, liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers* in *Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the carbohydrate can be incorporated and the microspheres, or composite of microspheres, implanted for slow release over a period of time, ranging from days to months. See, for example, U.S. Pat. Nos. 4,906,474, 4,925,673, and 3,625,214.

The carbohydrates should be active when administered parenterally in amounts above about 1 μg/kg of body weight. For treatment of most inflammatory disorders, the dosage range will be between 0.1 to 30 mg/kg of body weight. A dosage of 70 mg/kg may be required for some of the carbohydrates characterized in the examples.

The criteria for assessing response to therapeutic modalities employing antibodies or carbohydrate is dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Modifications and variations of the present invention, methods for modulating binding reactions involving P-selectin using carbohydrate derived from or forming a portion of the P-selectin ligand, or antibodies to the ligand, will be obvious to those skilled in the art from the foregoing detailed description. Such modifications and variations are intended to come within the scope of the appended claims.

We claim:

1. A method for inhibiting an inflammatory response, comprising:

administering an effective amount of an antibody to a protein component or to a carbohydrate-protein component of P-selectin glycoprotein ligand, the glycoprotein ligand comprising a fucosylated sialylated glycoprotein containing sialyl Lewis$^x$ antigen and the glycoprotein ligand having an apparent relative molecular weight of 120,000 as assessed by SDS-PAGE under reducing conditions and wherein the antibody has binding specific for P-selectin glycoprotein ligand and wherein the antibody inhibits binding of P-selectin glycoprotein ligand to P-selectin.

2. A method for inhibiting leukocyte adhesion, comprising:

administering an effective amount of an antibody to a protein component or to a carbohydrate-protein component of P-selectin glycoprotein ligand, the glycoprotein ligand comprising a fucosylated sialylated glycoprotein containing sialyl Lewis$^x$ antigen and the glycoprotein ligand having an apparent relative molecular weight of 120,000 as assessed by SDS-PAGE under reducing conditions and wherein the antibody has binding specific for P-selectin glycoprotein ligand and wherein the antibody inhibits binding of P-selectin glycoprotein ligand to P-selectin.

* * * * *